United States Patent [19]

Kasai et al.

[11] Patent Number: 4,507,415

[45] Date of Patent: Mar. 26, 1985

[54] MEDICAL ARTICLES

[75] Inventors: Masaaki Kasai, Zama; Toshiji Ichikawa, Chofu; Kimiho Kosegaki, Yokkaichi, all of Japan

[73] Assignee: Terumo Kabushiki Kaisha, Tokyo, Japan

[21] Appl. No.: 478,073

[22] Filed: Mar. 23, 1983

[30] Foreign Application Priority Data

Mar. 27, 1982 [JP] Japan .................................. 57-48159
Mar. 27, 1982 [JP] Japan .................................. 57-48160

[51] Int. Cl.$^3$ ............................................. C08K 5/34
[52] U.S. Cl. ................................... 524/101; 524/102; 524/108; 524/128; 524/342; 528/289; 204/159.18; 204/159.2; 424/78; 604/8; 604/403
[58] Field of Search .................. 204/159.18, 159.2; 524/101, 102, 108, 128, 342; 528/289

[56] References Cited

U.S. PATENT DOCUMENTS

| | | | |
|---|---|---|---|
| 3,196,185 | 7/1965 | Ranson | 524/342 |
| 3,356,770 | 12/1967 | Larrison | 524/128 |
| 3,476,699 | 11/1969 | Kauder et al. | 524/114 |
| 3,940,325 | 2/1976 | Hirao | 524/232 |
| 4,210,577 | 7/1980 | Minagawa et al. | 524/103 |
| 4,221,700 | 9/1980 | Minagawa et al. | 524/128 |
| 4,233,412 | 11/1980 | Rody et al. | 528/289 |
| 4,314,039 | 2/1982 | Kawai et al. | 524/108 |
| 4,401,536 | 8/1983 | Lundell et al. | 204/159.2 |

FOREIGN PATENT DOCUMENTS

0007736  6/1980  European Pat. Off. .

OTHER PUBLICATIONS

Norman S. Allen, "Catalytic Thermal Oxidation of Phenolic Antioxidants By Hindered Piperidine Compounds, "Polymer Degradation and Stability 3(1980-81), 73-81.

Khirud B. Chakraborty et al., "Mechanisms of Antioxidant Action: The Behaviour of Hindered Piperidine u.v. Stabilizers during the Processing of LDPE", Chemistry & Industry, 237-238, Apr. 1, 1978.

J. L. Williams et al., "Stability of Gamma Irradiated Polypropylene Part I. Mechanical Properties", Polymer Preprints—vol. 18, No. 1, Mar. 1977, 410-413.

T. S. Dunn et al., "Stability of Gamma Irradiated Polypropylene Part II. Electron Spin Resonance Studies", Polymer Preprints—vol. 18, No. 1, Mar. 1977, 414-419.

J. Reid Shelton, "Stabilization Fundamentals in Thermal Autoxidation of Polymers", Stabilization and Degradation of Polymers—David Allara et al., American Chemical Society, Wash. D.C., pp. 215-225, 1978.

*Primary Examiner*—John Kight
*Assistant Examiner*—Garnette D. Draper
*Attorney, Agent, or Firm*—Frishauf, Holtz, Goodman & Woodward

[57] ABSTRACT

Irradiation-sterilizable medical articles molded from a propylene polymer composition in which stabilizers are incorporated. Said composition comprises from 0.01 to 0.4 part by weight of each of a specific hindered amine and a specific phenol or its phosphite ester compound incorporated per 100 parts by weight of a propylene polymer with a weight-average molecular-weight to number-average molecular-weight ratio of 5 or below. The above-mentioned composition may additionally contain a sorbitol derivative as the nucleating agent. Medical articles produced from said composition by molding, for example, syringes are suitable for irradiation sterilization. Said medical articles when irradiated undergo little reduction in quality of the material and are accompanied by little bleeding or degradation of the incorporated stabilizers and nucleating agent.

15 Claims, No Drawings

MEDICAL ARTICLES

BACKGROUND OF THE INVENTION

1. Field of the Invention

This invention relates to irradiation-sterilizable medical articles.

More particularly, it is concerned with irradiation-sterilizable medical articles molded from propylene polymer compositions in which stabilizers are incorporated.

Propylene polymers, which have characteristic transparency, rigidity, impact strength and other properties, are widely used for medical articles, especially for disposable medical articles such as syringes, needle bases, infusion or blood transfusion sets, and instruments for blood collection. Propylene polymer products, however, have a disadvantage of being deteriorated or degraded by irradiation sterilization. When subjected to radiation at a dose from 2 to 4 Mrad., propylene polymers will undergo degradation or deterioration reactions thereby causing discoloration, cracking, reduction in impact strength in the product. Moreover, there will occur such problems as elution of the stabilizers incorporated into the polymer for inhibition of the oxidation, removal of the radicals and other objectives, development of odors and marked coloration. If the medical article is a product of injection molding, the deterioration caused by irradiation as set forth above will be especially remarkable.

2. Description of the Prior Art

Several processes have heretofore been reported for improving radiation resistance of the propylene polymer products.

It has been proposed to incorporate into the propylene polymers a variety of phenol, phosphorus or sulfur compounds as the stabilizer (U.S. Pat. No. 3,940,325), to incorporate hindered amines (European Patent Laid Open No. 7736) and to incorporate non-crystalline additives into propylene polymers with a narrower molecular weight distribution (U.S. Pat. No. 4,274,932). Although the radiation resistance of propylene polymers are considerably improved by these methods, there remains room for further improvement.

As a matter of fact, the incorporation of phenol, phosphorus or sulfur compounds is not satisfactory for practical use in coloration resistance, resistance to heat deterioration, as well as due to the elution phenomenon into the content that is contacted with the molded article. For example, the product to which tetrakis[methylene(3,5-di-t-butylhydroxyhydrocinnamate)]methane described in the above-mentioned U.S. Pat. No. 3,940,325 is added will be remarkably colored by gamma irradiation at a dose of 2.5 Mrad. The product to which 1,1,3-tris(2-methyl-5-t-butyl-4-hydroxyphenol)butane is added will also have unsatisfactory heat resistance after irradiated.

Addition of hindered amines, for example, di-(2,2,6,6-tetramethyl-4-piperidyl) sebacate, a hindered amine described in the above-mentioned European Patent Laid Open No. 7736 is associated with such problems as elution of the cytotoxic substances and bleeding of such additive onto the surface of the molded article during aging. Addition of the hindered amine alone will also result in reduction in molecular weight during molding thereby much decreasing the strength.

Also, the incorporation of non-crystalline additives in propylene polymers of a narrower molecular weight distribution is not practically usable because of unsatisfactory inhibition of deterioration as well as due to problematic bleeding and toxicity of the additives.

As described above, any of the heretofore reported processes have disadvantages in some respects so that they are not satisfactory for commercial use.

It is a general procedure to add a nucleating agent to propylene polymer compositions for improving transparency of the product. Dibenzylidenesorbitol, which is a nucleating agent excellent in transparency-improving effect among the nucleating agents presently available, will be degraded by irradiation and develop odors. Therefore, irradiation sterilization of medical articles containing this nucleating agent has not been acceptable.

SUMMARY OF THE INVENTION

It is therefore an object of the present invention to provide medical articles made of propylene polymers for which irradiation sterilization is commercially feasible.

The object of the invention is to provide propylene polymer medical articles satisfactory in every respect of safety and hygiene including toxicity and development of odors while maintaining such characteristics as transparency, rigidity and impact resistance.

According to the present invention, there are provided irradiation-sterilizable medical articles molded from a composition comprising as the stabilizers from 0.01 to 0.4 part by weight of a hindered amine represented by the formula [I] or [II] below and from 0.01 to 0.4 part by weight of a phenol or its phosphite ester compound represented by the formula [III], [IV] or [V] below per 100 parts by weight of a propylene polymer with a weight-average molecular-weight to number-average molecular-weight ratio of 5 or below.

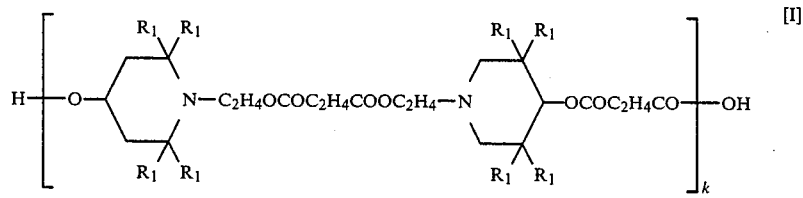

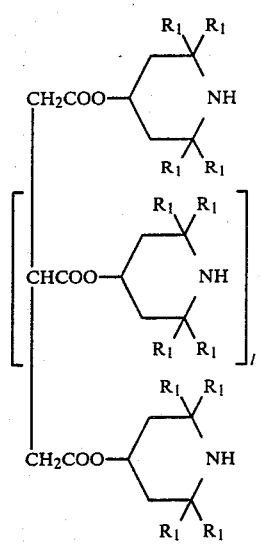

[II]

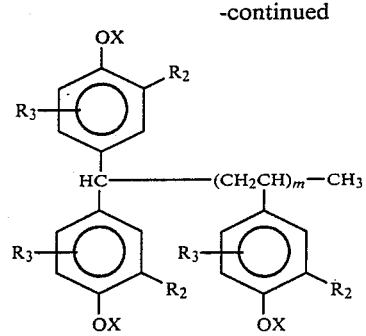

[III]

-continued

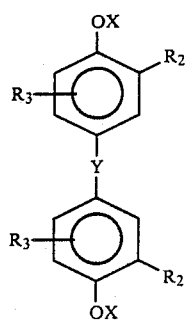

[IV]

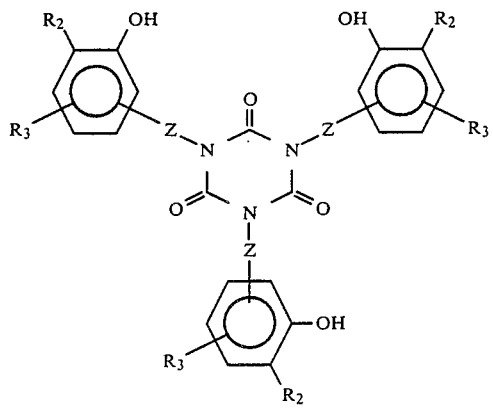

[V]

wherein:
$R_1$ represents an alkyl group containing 1–12 carbon atoms;
$R_2$ represents an alkyl group containing 3–12 carbon atoms;
$R_3$ represents an alkyl group containing 1–18 carbon atoms;
X represents hydrogen atom or the group

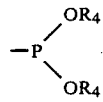

in which $R_4$ is an alkyl group containing 1–30 carbon atoms;
Y represents a divalent hydrocarbon radical containing 1–18 carbon atoms or sulfur atom;
Z represents a divalent hydrocarbon radical containing 1–8 carbon atoms in which a carbonyloxy group may be interposed;
k is an integer of 1–10;
l is an integer of 1–16; and
m is an integer of 1–6.

According further to the invention, there are provided radiation-sterilizable medical articles molded from a composition additionally containing from 0.01 to 0.4 part by weight of a compound represented by the formula [VI] below as the nucleating agent in the aforementioned propylene polymer compositions.

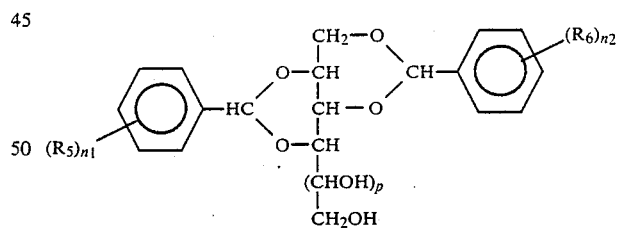

[VI]

wherein $R_5$ and $R_6$ each represent an alkyl or alkoxy group containing 1–8 carbon atoms, hydroxyl group or a halogen atom, $n_1$ and $n_2$ each independently represent an integer of 1–3 and p is 0 or 1.

DETAILED DESCRIPTION OF THE INVENTION

Medical articles of the invention are molded products of a composition containing as the stabilizers from 0.01 to 0.4 part by weight of a hindered amine represented by the above-described formula [I] or [II] and from 0.01 to 0.4 part by weight of a phenol or its phosphite ester compound represented by the above-described formula [III], [IV] or [V] per 100 parts by weight of a propylene polymer with a weight-average molecular-weight to number-average molecular-weight ratio (which is referred to as Q value hereinbelow) of 5 or below.

Furthermore, the medical articles of the invention are molded products from a composition comprising the aforementioned propylene polymer composition to which from 0.01 to 0.4 part by weight of a compound represented by the above-described formula [VI] is added as the nucleating agent.

In the medical articles of the invention are employed propylene polymers with a Q value of 5 or below, preferably from 2.5 to 4.8. The Q value represents molecular weight distribution, and the less is the Q value, the narrower will be the molecular weight distribution. Propylene polymers with a Q value greater than 5 are not suitable for use in the present invention due to too much reduction in impact strength when subjected to irradiation sterilization. The Q value can be controlled by a per se known method. Propylene polymers with a desired Q value are produced by such means as, for example, selection of the catalyst used in the preparation of the propylene polymer, process for feeding the monomer or selection of the polymerization conditions including pressure and temperature, or by pyrolysis of the produced powders when pelletized or degradation by the addition of a peroxide.

The propylene polymers as referred to in the present invention include propylene-ethylene copolymers containing 5% by weight or below of ethylene and blends of a propylene homopolymer and a propylene-ethylene copolymer containing in the blend 5% by weight or below of ethylene, in addition to polymers of propylene alone, namely, propylene homopolymers. The copolymers may be either random or block copolymers, although random copolymers are preferable. As the propylene homopolymer has a high rigidity when molded, it is desirable to control rigidity of the molded product for medical use for which flexibility is required for copolymerizing a small amount of ethylene as set forth above. The melt flow index (MFR) of the polymer is suitably from about 5 to 30 g./10 min. depending upon nature of the product. For example, it is desirable to employ the polymer with an ethylene content of 1.5-3.0% by weight and an MFR of 10-20 for the mantle of the syringe and with an ethylene content of 0-3.0% by weight and an MFR of 6-20 for the hub of the syringe needle and the connector having an air trap structure in the infusion set.

As preferred examples of the hindered amine employed as the stabilizer are mentioned compounds of the formula [I] wherein $R_1$ is methyl and k is 3–4, and compounds of the formula [II] wherein $R_1$ is methyl and l is 2. Combinations of two or more hindered amines of the formula [I] or [II] may be used in the present invention. The hindered amines are incorporated in a proportion of 0.01 to 0.4, preferably 0.03–0.3 part by weight per 100 parts by weight of the propylene polymer.

Preferred examples of another stabilizer, the phenol or its phosphite ester compounds include compounds of the formula [III] wherein $R_2$ is t-butyl (5-position), $R_3$ is methyl (2-position), X is hydrogen atom and m is 1, $R_2$ is t-butyl (5-position), $R_3$ is methyl (2-position), X is the group $-P(OC_{18}H_{37})_2$ and m is 1, compounds of the formula [IV] wherein $R_2$ is t-butyl (5-position), $R_3$ is methyl (2-position), X is hydrogen atom and Y is the group $<CH-CH_2-CH_2-CH_3$, or $R_2$ is t-butyl (5-position), $R_3$ is methyl (2-position), X is hydrogen and Y is $-S-$ or $R_2$ is t-butyl (5-position), $R_3$ is methyl (2-position), X is the group $-P(OC_{18}H_{37})_2$ and Y is the group $-CH-CH_2-CH_2-CH_3$, and compounds of the formula (V) wherein $R_2$ and $R_3$ each are t-butyl (3- and 5-positions) and Z is methylene, or $R_2$ and $R_3$ each are t-butyl (3- and 5-positions) and Z is the group $-CH_2CH_2COOCH_2CH_2-$. Combinations of two or more phenol or its phosphite ester compounds of the formula [III], [IV] or [V] may also be used in the present invention. The phenol or its phosphite ester compounds are incorporated in a proportion of 0.01–0.4, preferably 0.03–0.3 part by weight per 100 parts by weight of the propylene polymer.

As a preferred example of the nucleating agent used in the medical articles of the invention is mentioned a compound of the formula [VI] wherein $R_5$ and $R_6$ each are methyl (4-position), $n_1$ and $n_2$ each are 1 and p is 1. The nucleating agent is incorporated in a proportion of 0.01–0.4, preferably 0.03–0.3 part by weight per 100 parts by weight of the propylene polymer.

To the composition of the invention thus obtained may be added other additives such as, for example, the antioxidant, light stabilizer, ultraviolet ray-absorbing agents, antistatic agent, neutralizing agent such as a metal soap, dispersing agent and pigment provided that they will not inhibit the objectives and results of the invention.

The medical articles according to the present invention are prepared by melt kneading the above-described composition in a kneader such as a roller, Banbury mixer, Brabender-plasticorder or extruder and molding into a medical article by means such as of injection molding. It is general procedures to incorporate additives into powdery propylene polymer, blend the mass in an appropriate blending equipment such as a mixer, melt knead the blend in an extruder into pellets and subject the pellets or directly without pelleting to injection molding. Irradiation sterilization is preferably carried out in the shipping form after the molded product is packaged, for example, in polyethylene film. The irradiation is effected by the use of γ- or X-ray, preferably γ-ray from a cobalt-60 source. The radiation dose is 5 Mrad. or below, preferably from 2 to 4 Mrad. Excessive irradiation will cause deterioration of the molded product. The irradiation may be made under vacuum, in an inert gas such as nitrogen or in air. The temperature employed is 80° C. or lower, preferably ordinary temperature or lower.

As examples of the medical articles obtained according to the invention are mentioned the syringe, the base for the syringe needle, the infusion or blood transfusion set and the instrument for blood collection, but they are not limited to the above-mentioned.

The invention will be described in more detail by cited examples and comparative examples.

EXAMPLE 1

To a powdery propylene-ethylene random copolymer were added a hindered and a phenol or its phosphite ester compound of the invention or used as a control in amounts incorporated as shown in Table 1. The blend was formed into pellets by means of an extruder 30 mm. in diameter (230° C.). In order to adjust the MFR (230° C., 2.16 kg) and the Q value to the values shown in Table 1, the base powder with an appropriate MFR was selected, and Perhexyne 25B [Trade name for 2,5-dimethyl-2,5-(di-t-butylperoxy)-hexyne-3] was added in preparing the predetermined pellets. The pellets thus obtained was placed in the injection molding machine IS90B manufactured by Toshiba Machinery to form a square sheet 100×100×1 mm. in size (280° C.). The sheet was subjected to gamma irradiation from a cobalt-60 source (2.5 Mrad.) and placed under evaluation.

Items for the evaluation included the degree of coloration by visual observation after placed in an oven at 80° C. for a week, the measurement of haze by means of a hazemeter (ASTM-D-1003), the measurement of energy at 50% breakage by means of a Dupon impact tester manufactured by Toyo Seiki, the measurement of days to cracking or embrittlement when placed in an oven at 120° C., the measurement of MFR for the test piece and the observation of bleeding on the surface after placed in an oven at 80° C.

A cytotoxicity test was carried out by extracting small test pieces with MFM medium in an amount three times as much at 121° C. for 20 minutes and microscopically examining toxicity of the extract against HeLa-S3 cells. The judgment was indicated as 0 for no difference from the blank, 1 for a slight increase of the dead cells, 2 for death of almost all the cells and 3 for death of all the cells. Hemolytic toxicity was tested by immersing a test piece with a surface area of 1,200 $cm^2$ in physiological saline solution at 121° C. for 20 minutes, adding clean rabbit red blood cells to the extract thus obtained, and allowing the mixture to stand at 37° C. for 24 horus. The judgment was made from the degree of coloration of the resulting solution. No difference from the blank was indicated as nontoxic (−), coloration to pale red as weakly toxic (±), coloration to red as toxic (+) and coloration to deep red as strongly toxic (+ +). Results are shown in Table 1.

Product of ICI.
  A compound of the formula [III], 1,1,3-tris(2-methyl-4-hydroxy-5-t-butylphenyl)butane.
Goodrite 3114
  Product of Goodrich Chemical.
  A compound of the formula [V], tris-(3,5-di-t-butyl-4-hydroxybenzyl)isocyanurate.
Mark 522A
  Product of Adeka Argus Chemical Co.
  A compound of the formula [III] in which R=t-butyl (5-position), $R_3$=methyl (2-position), X=

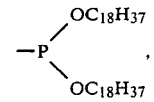

m=1.
Irganox 1010
  Product of Ciba-Geigy.
  Tetrakis[methylene-3-(3,5-di-t-butyl-4-hydroxyphenyl)-propionate]methane.
PBK
  Product of Nitto Chemical.
  Calcium stearate.

In Table 1, Examples 1, (1)–(3) relate to compositions of the present invention, namely, those in which a hindered amine and a phenol or its phosphite ester were incorporated as the stabilizers into a propylene polymer. Comparative Examwple 1-(1) relates to a composition in which a hindered amine of the invention alone but none of the phenol or its phosphite ester were incorporated, Comparative Example 1-(2) relates to a com-

TABLE 1

| | | Evaluation the injection-molded sheets 1 mm. in thickness. | | | | | | | |
|---|---|---|---|---|---|---|---|---|---|
| | | | Example 1 | | | Comparative Example 1 | | | |
| | | | (1) | (2) | (3) | (1) | (2) | (3) | (4) |
| Propylene polymer | MFR | g./10 min. | 15 | 15 | 15 | 15 | 15 | 15 | 15 |
| | Ethylene content | wt. % | 2.5 | 2.5 | 2.5 | 2.5 | 2.5 | 2.5 | 2.5 |
| | Q value | — | 4.4 | 4.4 | 4.4 | 4.4 | 4.4 | 5.4 | 5.4 |
| Hindered amine | Sanol LS622 | wt. % | 0.05 | 0.05 | 0.05 | 0.05 | — | — | — |
| | Sanol LS770 (control) | " | — | — | — | — | 0.2 | — | — |
| Phenol or its phosphite ester | Topanol CA | " | 0.03 | — | — | — | — | — | — |
| | Goodrite 3114 | " | — | 0.03 | — | — | 0.05 | — | — |
| | Mark 522A | " | — | — | 0.10 | — | — | — | — |
| | Irganox 1010 (control) | " | — | — | — | — | — | 0.03 | — |
| Adjunctive | PBK | " | 0.05 | 0.05 | 0.05 | 0.05 | 0.05 | 0.05 | 0.05 |
| Pre-gamma-irradiation | Degree of coloration (80° C., 1 wk.) | Visual | Colorless | Colorless | Colorless | Colorless | Colorless | Colorless | Colorless |
| | Haze | % | 40 | 40 | 39 | 40 | 40 | 40 | 45 |
| | Dupont impact strength | kg·cm | >30 | >30 | >30 | >30 | >30 | 4 | 7 |
| | Oven life (120° C.) | day | >10 | >10 | >10 | >10 | >10 | >10 | 1 |
| Post-gamma-irradiation | Degree of coloration (80° C., 1 wk.) | Visual | Colorless | Colorless | Colorless | Colorless | Pale yellow | Deep yellow | Colorless |
| | Dupont impact strength | kg·cm | 23 | 22 | 20 | 14 | 20 | <1 | <1 |
| | Oven life (120° C.) | day | >10 | >10 | >10 | >10 | >10 | 3 | <1 |
| | MFR | g./10 min. | 78 | 80 | 83 | >100 | >100 | >100 | >100 |
| | Bleeding (80° C., 1 wk.) | Visual | Absent | Absent | Absent | Absent | Present | Absent | Absent |
| | Hemolytic toxicity | | ⊖ | ⊖ | ⊖ | ⊖ | ⊕ | ⊕ | ⊕ |
| | Cytotoxicity | | 0 | 0 | 0 | 0 | 3 | 1 | 1 |

The stabilizers and adjunctives specified by the trade name in the table are compounds as indicated below.
Sanol LS622
  Product of Ciba-Geigy.
  A compound of the formula [I] wherein $R_1$=$CH_3$, k=3-4.
Sanol LS770
  Product of Sankyo Co., Ltd. which is chemically bis-(2,2,6,6-tetramethylpiperidyl)sebacate.
Topanol CA position in which a hindered amine beyond the scope of the invention was incorporated as the stabilizer, Comparative Example 1-(3) relates to a composition in which a phenol compound beyond the scope of the invention was incorporated as the stabilizer, and comparative Example 1-(4) relates to a composition in which none of the stabilizer was incorporated. From the results in Table 1, it can be seen that when gamma-irradiated, the injection-molded articles according to the invention do not undergo significant reduction in impact strength but there is observed marked reduction in the comparative examples. It is also obvious that whereas the molded products according to the present invention undergo almost no color change, color change to yellow is observed in the comparative examples and the color change is remarkable when a phenol compound beyond the scope of the invention is incorporated [Comparative Example 1-(3)].

Besides, it is demonstrated that when a hindered amine beyond the scope of the invention is employed [Comparative Example 1-(2)], cytotoxic substances are eluted.

EXAMPLE 2

Powders of the compositions shown in Table 2 were melt kneaded and formed into pellets. The pellets were formed using an injection molding machine into a mantle of the syringe having a cylindrical portion 17.7 mm. in outer diameter, 750 mm. in length and 0.98 mm. in thickness.

The syringe mantle was irradiated at a dose of 25 Mrad. using a cobalt-60 source.

The test materials were divided into 4 groups, a group non-irradiated, a group non-irradiated and allowed to stand in an air-circulation oven at 80° C. for 7 days, a group irradiated and allowed to stand at room temperature for 30 days and a group irradiated and allowed to stand in an air-circulation oven at 80° C. for 7 days. Measurements were made by the methods described below. Results are shown in Table 3. Color was judged by visual observation, and represented by ⊚ for non-color change, O for very slight yellow color change, Δ for slight yellow color change and X for yellow color change.

Potassium permanganate-reducing substances were measured according to the Standard for Disposable Syringe (Japanese Ministry of Health and Welfare) for the extract from the test pieces 1 cm² in size with distilled water in an amount 10 times as much at 121° C. for 20 minutes. They are indicated under ΔKMnO₄.

Bleeding was judged by visual observation. No bleeding is indicated as − and bleeding if observed as +.

Compression strength was determined by compressing the center of a syringe using a 7-mm. steal rod and measuring the load when fracture takes place. The measurement was made at 25° C. − in the table indicates no fracture.

Impact strength was determined in terms of 50% breakage energy according to JIS-K7211 by dropping a cylinder weighing 120 g. and 30 mm. in diameter from varied heights.

Cracking after irradiated was measured using a gear oven at 120° C. The presence or absence of cracks was visually examined.

Cytotoxicity was tested by the same method as in Example 1.

Sanol LS622, SAnol LS770, Topanol CA, Goodrite 3114, Irganox 1010 and PBK which are trade names shown in Table 2 are the same products as indicated in Table 1 in Example 1. Mark LA57 is a product of Adeka Argus Chemical Co., which is a compound of the formula [II] wherein $R_1=CH_3$ and $l=2$.

TABLE 2

| | Formula | | Example 2 | | | | | | Comparative Example 2 | | | | | | |
|---|---|---|---|---|---|---|---|---|---|---|---|---|---|---|---|
| | | | (1) | (2) | (3) | (4) | (5) | (6) | (1) | (2) | (3) | (4) | (5) | (6) | (7) |
| Propylene Polymer | Ethylene content | wt. % | 0 | 2.5 | 2.5 | 2.5 | 2.5 | 2.5 | 0 | 2.5 | 2.5 | 2.5 | 2.5 | 2.5 | 2.5 |
| | Q value | — | 4.4 | 4.4 | 4.4 | 4.4 | 4.4 | 4.4 | 5.4 | 5.4 | 4.4 | 4.4 | 5.4 | 4.4 | 4.4 |
| Hindered amine | Sanol LS622 | wt. % | 0.05 | 0.05 | 0.05 | — | 0.10 | 0.05 | 0.05 | 0.05 | — | — | — | — | — |
| | Mark LA57 | " | — | — | — | 0.05 | — | — | — | — | — | — | — | — | — |
| | Sanol LS770 (control) | " | — | — | — | — | — | — | — | — | — | — | — | 0.10 | 0.10 |
| Phenol or its phosphite ester | Topanol CA | " | 0.05 | 0.05 | — | 0.05 | 0.05 | 0.10 | 0.05 | 0.05 | — | 0.10 | 0.10 | — | 0.05 |
| | Goodrite 3114 | " | — | — | 0.05 | — | — | — | — | — | — | — | — | — | — |
| | Irganox 1010 (control) | " | — | — | — | — | — | — | — | — | 0.10 | — | — | — | — |
| Adjunctive | PBK | " | 0.05 | 0.05 | 0.05 | 0.05 | 0.05 | 0.05 | 0.05 | 0.05 | 0.10 | 0.10 | 0.10 | 0.05 | 0.05 |

TABLE 3

| | | Example 2 | | | | | | Comparative Example 2 | | | | | | |
|---|---|---|---|---|---|---|---|---|---|---|---|---|---|---|
| | | (1) | (2) | (3) | (4) | (5) | (6) | (1) | (2) | (3) | (4) | (5) | (6) | (7) |
| Start | Coloration | ⊚ | ⊚ | ⊚ | ⊚ | ⊚ | ⊚ | ⊚ | ⊚ | ⊚ | ⊚ | ⊚ | ⊚ | ⊚ |
| | ΔKMnO₄ (ml) | 0.18 | 0.28 | 0.22 | 0.31 | 0.29 | 0.19 | 0.13 | 0.23 | 0.15 | 0.22 | 0.23 | 0.28 | 0.28 |
| | Cytotoxicity | 0 | 0 | 0 | 0–1 | 0 | 0 | 0 | 0 | 0 | 0 | 0 | 2 | 2 |
| | Compression strength (kg · f) | 41.7 | — ° | — | — | — | — | 43.5 | — | — | — | — | — | — |
| | Impact strength (kg · f · cm) | 0.52 | >12 | >12 | >12 | >12 | >12 | 0.38 | 3.3 | >12 | >12 | 3.3 | >12 | >12 |
| No γ-Irradiation 7 days, 80° C. | Coloration | ⊚ | ⊚ | ⊚ | ⊚ | ⊚ | ⊚ | ⊚ | ⊚ | ⊚ | ⊚ | ⊚ | ⊚ | ⊚ |
| | Bleeding | − | − | − | − | − | − | − | − | − | − | − | − | − |
| | Compression strength (kg · f) | 32.5° | — | — | — | — | — | 38.3 | — | — | — | — ° | ° | — |
| | Impact strength (kg · f · cm) | 0.50 | >12 | >12 | >12 | >12 | >12 | 0.32 | 3.2 | >12 | >12 | 3.2 | >12 | >12 |
| 2.5 Mrad. irradiation | Coloration | O | O | ⊚ | O | O | O | O | O | X | O | O | O | O |
| | ΔKMnO₄ (ml) | 0.23 | 0.26 | 0.33 | 0.33 | 0.34 | 0.24 | 0.25 | 0.30 | 0.28 | 0.29 | 0.31 | 0.35 | 0.34 |
| | Cytotoxicity | 0 | 0 | 0 | 1 | 0 | 0 | 0 | 0 | 0 | 0 | 0 | 3 | 3 |

TABLE 3-continued

|  |  | Example 2 |  |  |  |  |  | Comparative Example 2 |  |  |  |  |  |  |
|---|---|---|---|---|---|---|---|---|---|---|---|---|---|---|
|  |  | (1) | (2) | (3) | (4) | (5) | (6) | (1) | (2) | (3) | (4) | (5) | (6) | (7) |
| 30 days, room temp. | Compression strength (kg · f) | 21.7 | 21.7 | 22.3 | 22.2 | 22.1 | 21.9 | 23.5 | 20.5 | 22.3 | 21.8 | 20.3 | 22.5 | 22.3 |
|  | Impact strength (kg · f · cm) | 0.49 | 6.3 | 5.8 | 6.2 | 6.1 | 5.9 | 0.31 | 1.2 | 5.3 | 5.2 | 0.9 | 5.8 | 5.9 |
| 2.5 Mrad. irradiation 7 days, 80° C. | Coloration | O | O | O | O | O | O-Δ | O | O | X | O-Δ | O-Δ | O | O |
|  | Bleeding | — | — | — | — | — | — | — | — | — | — | — | + | + |
|  | Compression strength (kg · f) | 18.9 | 18.8 | 17.3 | 18.5 | 18.9 | 17.3 | 18.5 | 19.2 | 18.9 | 16.5 | 16.2 | 18.9 | 18.5 |
|  | Impact strength (kg · f · cm) | 0.49 | 3.8 | 3.7 | 2.9 | 3.5 | 3.7 | 0.29 | 0.75 | 3.5 | 1.3 | 0.62 | 3.1 | 2.9 |
| 2.5 Mrad. irradiation, 120° C. | Time to crack development (hrs.) | >1000 | >1000 | >1000 | >1000 | >1000 | >1000 | >1000 | >1000 | >1000 | 47 | 48 | >1000 | >1000 |

The material used for the syringe mantle according to the present invention is quite satisfactory for use in coloration, bleeding, ΔKMnO$_4$, cytotoxicity and compression strength after irradiated and allowed to stand at 80° C. for 7 days. However, in view of the weak impact strength of the polypropylene containing no ethylene, it is desirable to employ a polypropylene containing ethylene as much as around 2.5% by weight for use as the syringe mantle. As the impact strength after irradiated is lowered even with polypropylenes containing ca. 2.5% by weight of ethylene if the Q value is 5 or higher, the Q value is 5 or below, most desirably around 4.4.

The test material in which Irganox 1010, an additive described in U.S. Pat. No. 3,940,325 [Comparative Example 2-(3)] is employed is highly colored and is hardly usable from the commercial point of view. The test materials in which Topanol CA described in the same U.S. Patent is employed [Comparative Examples 2-(4), (5)] are short in oven life and is not acceptable for practical use as medical articles. The test materials in which Sanol LS770 described in European Patent Laid Open No. 7736 is employed [Comparative Examples 2-(6), (7)] show high cytotoxicity and bleeding and are not suitable for medical articles.

Also, Comparative Example 2-(4) indicates that narrower molecular weight distribution only accerelates deterioration of the physical properties unless the stabilizers are combined in a proper manner.

EXAMPLE 3

To a powdery propylene-ethylene random copolymer were added a hindered, a phenol or its phosphite ester compound and a nucleating agent of the invention or used as a control in amounts incorporated as shown in Table 4. The blend was formed into pellets by means of an extruder 30 mm. in diameter (230° C.). In order to adjust the MFR (230° C., 2.16 kg.) and the Q value to the values shown in Table 4, the base powder with an appropriate MFR was selected, and Perhexyne 25B [Trade name for 2,5-dimethyl-2,5-(di-t-butylperoxy)-hexyne-3] was added in preparing the predetermined pellets. The pellets thus obtained was placed in the injection molding machine IS90B manufactured by Toshiba Machinery to form a square sheet 100×100×1 mm. in size (280° C.). The sheet was subjected to gamma irradiation from a cobalt-60 source (2.5 Mrad.) and placed under evaluation.

Items for the evaluation included the degree of coloration by visual observation after placed in an oven at 80° C. for a week, the measurement of haze by means of a hazemeter (ASTM-D-1003), the measurement of energy at 50% breakage by means of a Dupon impact tester manufactured by Toyo Seiki, the measurement of days to cracking or embrittlement when placed in an oven at 120° C., the measurement of MFR for the test piece and the observation of bleeding on the surface after placed in an oven at 80° C.

A cytotoxicity test was carried out by extracting small test pieces with MFM medium in an amount three times as much at 121° C. for 20 minutes and microscopically examining toxicity of the extract against HeLa-S3 cells. The judgment was indicated as 0 for no difference from the blank, 1 for a slight increase of the dead cells, 2 for death of almost all the cells and 3 for death of all the cells. Hemolytic toxicity was tested by immersing a test piece with a surface area of 1,200 cm$^2$ in physiological saline solution at 121° C. for 20 minutes, adding clean rabbit red blood cells to the extract thus obtained, and allowing the mixture to stand at 37° C. for 24 hours. The judgment was made from the degree of coloration of the resulting solution. No difference from the blank was indicated as nontoxic (−), coloration to pale red as weakly toxic (±), coloration to red as toxic (+) and coloration to deep red as strongly toxic (++). Results are shown in Table 4.

TABLE 4

| Evaluation using the injection-molded sheet 1 mm. in thickness. | | | | | | | | | | | | |
|---|---|---|---|---|---|---|---|---|---|---|---|---|
|  |  |  | Example 3 | | | | | Comparative Example 3 | | | | |
|  |  |  | (1) | (2) | (3) | (4) | (5) | (1) | (2) | (3) | (4) | (5) |
| Propylene polymer | MFR | g./10 min. | 15 | | 15 | | 15 | 15 | | | 15 | |
|  | Ethylene content | wt. % | 1.8 | | 2.0 | | 2.5 | 2.5 | | | 2.5 | |
|  | Q value | — | 4.0 | | 4.4 | | 4.4 | 4.4 | | | 5.4 | |
| Hindered amine | Sanol LS622 | wt. % | 0.05 | — | 0.05 | — | 0.05 | 0.05 | — | — | — | — |
|  | Mark LA57 | " | — | 0.05 | — | 0.1 | — | — | — | — | — | — |
|  | Sanol LS770 (control) | " | — | — | — | — | — | — | 0.1 | 0.2 | — | — |
| Phenol or its phosphite | Topanol CA | " | 0.03 | 0.03 | — | 0.04 | 0.03 | — | — | — | 0.04 | — |
|  | Goodrite 3114 | " | — | — | — | — | — | — | — | 0.05 | — | 0.04 |
|  | Mark 522A | " | — | — | 0.1 | — | — | — | — | — | — | — |

TABLE 4-continued

Evaluation using the injection-molded sheet 1 mm. in thickness.

|  |  |  | Example 3 ||||| Comparative Example 3 |||||
| --- | --- | --- | --- | --- | --- | --- | --- | --- | --- | --- | --- | --- |
|  |  |  | (1) | (2) | (3) | (4) | (5) | (1) | (2) | (3) | (4) | (5) |
| ester | Irganox 1010 (control) | " | — | — | — | — | — | — | — | — | — | — |
|  | DMTP | " | — | — | — | — | — | — | — | — | 0.15 | 0.05 |
| Nucleating agent | Gelall MD | " | 0.20 | 0.20 | 0.18 | 0.20 | 0.18 | — | — | — | — | — |
|  | ECl (control) | " | — | — | — | — | — | — | — | 0.18 | 0.25 | 0.18 |
| Adjunctive | PBK | " | 0.05 | 0.05 | 0.05 | 0.05 | 0.05 | 0.05 | 0.05 | 0.05 | 0.05 | 0.05 |
| Pre-gamma-irradiation | Coloration (80° C., after 1 wk.) | Visual | Colorless | Colorless | Colorless | Colorless | Colorless | Colorless | Colorless | Colorless | Colorless | Colorless |
|  | Haze | % | 9 | 7 | 9 | 8 | 9 | 40 | 40 | 18 | 14 | 19 |
|  | Dupont impact strength | kg · cm | >30 | >30 | >30 | >30 | >30 | >30 | >30 | 5 | 4 | 4 |
|  | Oven life (120° C.) | days | >10 | >10 | >10 | >10 | >10 | >10 | >10 | >10 | >10 | >10 |
| Post-gamma-irradiation | Coloration (80° C., after 1 wk.) | Visual | Colorless | Colorless | Colorless | Colorless | Colorless | Colorless | Colorless | Pale yellow | Yellow | Pale yellow |
|  | Dupont impact strength | kg · cm | 17 | 25 | 20 | 22 | 24 | 14 | 10 | <1 | <1 | <1 |
|  | Oven life (120° C.) | days | >10 | >10 | >10 | >10 | >10 | >10 | >10 | >10 | 4 | <1 |
|  | MFR | g./10 min. | 73 | 58 | 74 | 69 | 77 | >100 | 94 | >100 | >100 | >100 |
|  | Bleeding (80° C., after 1 wk.) | Visual | Absent | Absent | Absent | Absent | Absent | Absent | Present | Present | Absent | Absent |
|  | Hemolytic toxicity |  | ⊖ | ⊖ | ⊖ | ⊖ | ⊖ | ⊖ | ± | ⊖ | ⊕ | ⊕ |
|  | Cytoxicity |  | 0 | 0 | 0 | 1 | 0 | 0 | 3 | 3 | 1 | 1 |

Stabilizers, nucleating agents and adjunctives shown by the trade names in Table 4 represent the following compounds, respectively:

Sanol LS622, Sanol LS770, Topanol CA, Goodrite 3114, Mark 522A, Irganox 1010 and PBK are the same as shown in Table 1 in Example 1 and Mark LA57 is the same as shown in Table 2 in Example 2.

DMTP
Product of Yoshitomi Pharmaceutical.
Dimyristyl thiodipropionate.

Gelall MD
Product of ICI.
A compound of the formula [VI] wherein $R_5$ and $R_6$ each are methyl (4-position) and $n_1$ and $n_2$ each are 1 (1,3,2,4-di-p-methylbenzylidene-sorbitol).

ECl
Product of ICI.
1,3,2,4-Dibenzylidene-sorbitol.

Examples 3, (1)–(5) relate to compositions according to the present invention, that is, the incorporation of stabilizers and a nucleating agent according to the invention into propylene polymers. Comparative Example 3-(1) indicates an example in which a hindered amine of the invention alone was incorporated as the stabilizer but none of the phenol or its phosphite ester and the nucleating agent as in the invention was incorporated. Comparative Example 3-(2) indicates an example in which a hindered amine beyond the scope of the invention was incorporated. Comparative Example 3, (3)–(5) indicate examples in which into a propylene polymer having a Q value of 5 or higher was incorporated a phenol or its phosphite ester according to the invention but none of the hindered amines of the invention.

It is seen from the results in Table 4 that when gamma-irradiated, the injection-molded articles according to the invention do not undergo significant reduction in impact strength but there is observed marked reduction in the comparative examples. It is also obvious that whereas the molded products according to the present invention undergo almost no color change, color change to yellow is observed in the comparative examples. It is also indicated that compositions of the invention are superior in toxicity and inhibition of molecular-weight reduction.

EXAMPLE 4

Pellets of the compositions listed on Table 5 were prepared in the same way as in Example 3 except that an extruder 50 mm. in diameter (230° C.) was used. The pellets thus obtained were subjected to injection molding (280° C.) using Nestal 350T injection molding machine manufactured by Sumitomo Heavy Machinery to form a syringe mantle 10 ml in inner volume. It was gamma-irradiated as in Example 3. In addition to the evaluation items set forth in Table 4 in Example 3, transparency was evaluated by visual observation. Compression test was carried out by heat-treating the syringe mantle in an oven at 80° C. for a period of predetermined days and subsequently pressing the syringe mantle at the center with a rod 5 mm. in radius at a speed of 50 mm./min. Breakage when the diameter of the syringe (outer diameter 17 mm.) was decreased to about a half was observed using an autograph tester. When at least one of the three test samples was broken, the result was judged as broken. The odor was tested by placing a syringe mantle in polyethylene film 20μ in thickness, tightly closing and gamma-irradiating the film. Thirty days after the irradiation, the closure was opened and a sensibility test was made by human sense of small to judge the presence or absence of odor. Furthermore, in order to evaluate state of the syringe surface, measurement was made on the content angle between the syringe surface and a silicone drop (polydimethylsiloxane, 3000 cst). This was taken as a criterion for evaluating the bleeding of the degradates onto the surface. Results are shown in Table 5.

TABLE 5

Evaluation of the molded syringe mantle 10 ml in inner volume.

|  |  |  | Example 4 || Comparative Example 4 ||||
| --- | --- | --- | --- | --- | --- | --- | --- | --- |
|  |  |  | (1) | (2) | (1) | (2) | (3) | (4) | (5) |
| Propylene polymer | MFR | g./10 min. | 15 | 15 | 15 | 15 |  |  | 15 |

TABLE 5-continued

Evaluation of the molded syringe mantle 10 ml in inner volume.

| | | | Example 4 | | Comparative Example 4 | | | | | | | | | | |
|---|---|---|---|---|---|---|---|---|---|---|---|---|---|---|---|
| | | | (1) | | (2) | | (1) | | (2) | | (3) | | (4) | | (5) |
| | Ethylene content | wt. % | 1.8 | | 2.5 | | | | 2.5 | | | | | | 2.5 |
| | Q value | — | 4.0 | | 4.4 | | | | 4.4 | | | | | | 5.4 |
| Hindered amine | Sanol LS622 | wt. % | — | | 0.05 | | 0.05 | | 0.10 | | — | | — | | — |
| | Mark LA57 | " | 0.05 | | — | | — | | — | | — | | — | | — |
| | Sanol LS770 (control) | " | — | | — | | — | | — | | 0.05 | | — | | — |
| Phenol or its phosphite ester | Topanol CA | " | 0.03 | | 0.03 | | 0.03 | | 0.04 | | 0.03 | | 0.04 | | 0.04 |
| | DMTP | " | — | | — | | — | | — | | — | | 0.15 | | 0.15 |
| Nucleating agent | Gelall MD | " | 0.20 | | 0.18 | | — | | — | | — | | — | | — |
| | ECl (control) | " | — | | — | | 0.18 | | — | | 0.18 | | 0.18 | | 0.25 |
| Adjunctive | PBK | " | 0.05 | | 0.05 | | 0.05 | | 0.05 | | 0.05 | | 0.05 | | 0.05 |
| Physical properties of the molded syringe | | | gamma-irradiation | | | | | | gamma-irradiation | | | | | | | |
| | | | Pre | Post | Pre | Post | Pre | Post | Pre | Post | Pre | Post | Pre | Post | Pre | Post |
| Coloration (80° C., after 1 wk.) | | Visual[1] | C | A | C | A | C | A | C | A | C | A | C | P | C | P |
| Transparency | | Visual[2] | E | E | E | E | G | G | P | P | G | P | G | G | E | E |
| Compression strength test | 80° C., Start | NB: Not broken B: Broken | NB | NB | NB | NB | NB | NB | NB | NB | NB | NB | NB | B | NB | B |
| | After 1 wk. | | " | " | " | " | " | " | " | " | " | " | " | " | " | " |
| | After 2 wks. | | " | " | " | " | " | " | " | " | " | " | " | " | " | " |
| | After 3 wks. | | " | " | " | " | " | " | " | " | " | B | " | " | " | " |
| Oven life (120° C.) | | days | >10 | >10 | >10 | >10 | >10 | >10 | >10 | >10 | >10 | >10 | >10 | 1 | >10 | 1 |
| Bleeding (80° C., after 1 wk.) | | Visual[3] | A | A | A | A | A | A | A | A | P | P | A | A | A | A |
| Odor | | Smell[4] | W | W | W | W | W | S | W | W | W | S | W | S | W | S |
| Contact angle with a silicone drop | | Degree | — | — | 8.7 | 9.3 | 10.2 | 26.0 | — | — | — | — | — | — | — | — |
| Toxicity | Hemolitic toxicity | | — | — | — | — | — | — | — | — | ± | ± | ± | ± | ± | ± |
| | Cytotoxicity | | 0 | 0 | 0 | 0 | 0 | 1 | 0 | 0 | 2 | 3 | 0 | 1 | 0 | 1 |

[1]C: Colorless, A: Almost colorless, P: Pale yellow.
[2]E: Excellent, G: Good, P: Poor.
[3]A: Absent, P: Present.
[4]S: Strong, W: Weak.

In Table 5, Examples 4-(1) and (2) are test examples on molded products according to the present invention, that is, molded products of a propylene-ethylene random copolymer (Q value 5 or below) in which stabilizers and a nucleating agent according to the invention are incorporated. Comparative Examples 4, (1)–(5) indicate test examples of the incorporation of a nucleating agent beyond the scope of the invention. The results in Table 5 demonstrate that the molded products according to the invention are superior in all of the evaluation items, coloring, transparency, compression strength, oven life, bleeding, odor, contact angle with a silicone drop and toxicity and may be put to practical use as medical articles resistant to radiation.

The contact angle with a silicone drop in the above tests represents bleeding of the additives onto the surface of the molded product. Whereas in Example 4-(2) little increase in the contact angle is observed after the irradiation, a big increase is observed in Comparative Example 4-(1). This difference indicates that bleeding of hydrophilic substances onto the surface took place with the incorporation of ECl, which substances repelled silicone.

EXAMPLE 5

Powders of the compositions shown in Table 6 were melt kneaded and formed into pellets. The pellets were formed using an injection molding machine into a mantle of the syringe having a cylindrical portion 17.7 mm. in outer diameter, 750 mm. in length and 0.98 mm. in thickness.

The syringe mantle was irradiated at a dose of 2.5 Mrad. using a cobalt-60 source.

The test materials were divided into 4 groups, a group non-irradiated, a group non-irradiated and allowed to stand in an air-circulation oven at 80° C. for 7 days, a group irradiated and allowed to stand at room temperature for 30 days and a group irradiated and allowed to stand in an air-circulation oven at 80° C. for 7 days. Measurements were made by the methods described below. Color was judged by visual observation, and represented by ⊙ for non-color change, O for very slight yellow color change, Δ for slight yellow color change and X for yellow color change.

Potassium permanganate-reducing substances were measured according to the Standard for Disposable Syringe (Japanese Ministry of Health and Welfare) for the extract from the test pieces 1 cm² in size with distilled water in an amount 10 times as much at 121° C. for 20 minutes. They are indicated under ΔKMnO₄.

Bleeding was judged by visual observation. No bleeding is indicated as − and bleeding if observed as +.

Compression strength was determined by compressing the center of a syringe using a 7-mm. steal rod and measuring the load when fracture takes place. The measurement was made at 25° C. — in the table indicates no fracture.

Impact strength was determined in terms of 50% breakage energy according to JIS-K7211 by dropping a cylinder weighing 120 g. and 30 mm. in diameter from varied heights.

Cracking after irradiated was measured using a gear oven at 120° C. The presence or absence of cracks was visually examined. The odor on opening the package was referred to as ⊙ for odorles, O for slight odor, Δ for moderate odor and X for offensive odor. Transparency was evaluated by the measurement of haze according to ASTM (D-1003) on the sheet 1 mm. in thickness molded from the composition. Cytotoxicity and hemolytic toxicity were tested by the same method as in Example 3. Results are shown in Table 6.

TABLE 6

|  |  |  | Example 5 | | | Comparative Example 5 | | | |
| --- | --- | --- | --- | --- | --- | --- | --- | --- | --- |
|  |  |  | (1) | (2) | (3) | (1) | (2) | (3) | (4) |
| Propylene polymer | Ethylene content | wt. % | 0 | 2.5 | 2.5 | 0 | 0 | 2.5 | 2.5 |
|  | Q value | — | 4.4 | 4.4 | 4.4 | 4.4 | 4.4 | 4.4 | 4.4 |
| Stabilizer | Sanol LS622 | wt. % | 0.05 | 0.05 | 0.05 | 0.05 | 0.05 | 0.05 | 0.05 |
|  | Topanol CA | " | 0.03 | 0.03 | 0.03 | 0.03 | 0.03 | 0.03 | 0.03 |
| Nucleating agent | Gelall MD | " | 0.2 | 0.18 | 0.18 | — | — | — | — |
|  | ECI (control) | " | — | — | — | — | 0.2 | — | 0.2 |
| Adjunctive | PBK | " | 0.05 | 0.05 | 0.05 | 0.05 | 0.05 | 0.05 | 0.05 |
| Start | Coloration |  | ◎ | ◎ | ◎ | ◎ | ◎ | ◎ | ◎ |
|  | Haze (%) |  | 9 | 9 | 9 | — | — | 40 | 18 |
|  | ΔKMnO$_4$ (ml) |  | 1.12 | 1.12 | 0.89 | 0.15 | 3.51 | 0.21 | 3.89 |
|  | Cytotoxicity |  | 0 | 0 | 0 | 0 | 0 | 0 | 0 |
|  | Compression strength (kg · f) |  | 41.5 | — | — | 42.1 | 42.3 | — | — |
|  | Impact strength (kg · f · cm) |  | 0.29 | >12 | >12 | 0.32 | 0.35 | >12 | >12 |
| No γ-irradiation, | Coloration |  | ◎ | ◎ | ◎ | ◎ | ◎ | ◎ | ◎ |
| 80° C., after 7 days | Bleeding |  | — | — | — | — | — | — | — |
|  | Compression strength (kg · f) |  | 36.5 | — | — | 37.3 | 38.5 | — | — |
|  | Impact strength (kg · f · cm) |  | 0.25 | >12 | >12 | 0.28 | 0.32 | >12 | >12 |
| 2.5 Mrad. | Coloration |  | O | O | O | O | O | O | O |
| irradiation, | Haze (%) |  | 9 | 9 | 9 | — | — | 39 | 17 |
| room temp., | Odor |  | O | O | O | O | X | O | X |
| after 30 days | ΔKMnO$_4$ (ml) |  | 1.28 | 1.31 | 0.98 | 0.23 | 3.63 | 0.32 | 4.02 |
|  | Cytotoxicity |  | 0 | 0 | 0 | 0 | 0 | 0 | 0 |
|  | Compression strength (kg · f) |  | 24.2 | 22.3 | 21.2 | 25.3 | 23.8 | 22.3 | 21.8 |
|  | Impact strength (kg · f · cm) |  | 0.29 | 6.2 | 6.1 | 0.32 | 0.33 | 6.3 | 5.9 |
| 2.5 Mrad. | Coloration |  |  |  |  |  |  |  |  |
| irradiation, | Bleeding |  | — | — | — | — | — | — | — |
| 80° C., | Compression strength (kg · f) |  | 19.2 | 18.6 | 17.5 | 18.5 | 18.6 | 17.9 | 18.3 |
| after 7 days | Impact strength (kg · f · cm) |  | 0.29 | 2.8 | 3.2 | 0.32 | 0.32 | 3.8 | 3.7 |
| 2.5 Mrad. irradiation, 120° C. | Time to crack development (hrs.) |  | >1000 | >1000 | >1000 | >1000 | >1000 | >1000 | >1000 |

Examples 5, (1)–(3) in Table 6 are test examples on molded products according to the present invention, that is, molded products of a propylene polymer with a Q value of 4.4 in which stabilizers and a nucleating agent according to the invention were incorporated. Comparative Examples 5-(2) and (4) refer to examples of the incorporation of a nucleating agent beyond the scope of the invention into a propylene polymer with a Q value of 4.4. Comparative Examples 5-(1) and (3) refer to examples of the incorporation of stabilizers according to the invention but none of the nucleating agent. The results in Table 6 demonstrate that the molded products according to the invention produce good results for all of the evaluation items and especially, for elution of potassium permanganate-reducing substances (ΔKMnO$_4$) and development of odor use of the nucleating agent according to the invention produce much superior results to those for the control.

According to the present invention, there are provided propylene polymer medical articles for which radiation sterilization is commercially feasible.

Firstly according to the invention, there are provided medical articles which undergo little reduction in strength of the material by radiation sterilization. Although the quality of propylene polymers is much deteriorated by radiation, the molded products in which the stabilizers according to the invention are incorporated undergo so small reduction in impact, compression and other strengths that they are satisfactorily useful as medical articles.

Secondly according to the invention, there are provided medical articles which are free from color change by irradiation. Some of the known stabilizers undergo degradation by irradiation to cause color change of the products. Such stabilizers cannot used in medical articles however good are the deterioration-inhibiting activities.

Thirdly according to the invention, there are provided safe medical articles which are free from bleeding of the additives or elution of toxic degradates. Some of the prior-art stabilizers have a tendency to cause bleeding on the surface of products on aging or are degraded by irradiation to yield toxic substances which will be eluted in the content in contracts with the medical article. As indicated above, such phenomena are not observed at all with the stabilizers used in the present invention.

Fourthly according to the invention, there are provided medical articles which undergo little reduction in strength of the material or transparency by irradiation. Although quality of propylene polymers are much deteriorated by irradiation, the molded products in which the stabilizers and nucleating agents according to the invention are incorporated not only undego reduction in impact, compression and other strengths but also maintain the transparency, and are satisfactorily useful as medical articls.

Fifthly according to the invention, there are provided medical articles which produce no odor by irradiation. Some of the prior-art nucleating agents which are incorporated into propylene polymer products in order to improve transparency are decomposed by irradiation to produce a bad odor. The nucleating agents used in the present invention produce no bad odor.

As described above, the present invention enables us to provide irradiation-sterilizable medical articles by incorporating specific stabilizers and nucleating agents skillfully selected into propylene polymers with a specific molecular-weight distribution and molding the resulting compositions.

What we claim is:

1. An irradiation-sterilizable medical article molded from a composition comprising as the stabilizers from 0.01 to 0.4 part by weight of a hindered amine represented by the formula [I] or [II] below and from 0.01 to 0.4 part by weight of a phenol or its phosphite ester compound represented by the formula [III], or [V]

below per 100 parts by weight of a propylene polymer with a weight-average molecular-weight to number-average molecular-weight ratio of 5 or below.

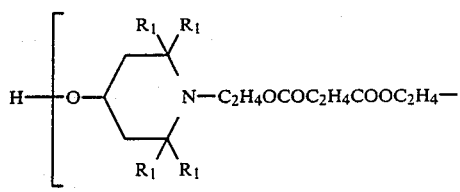  [I]

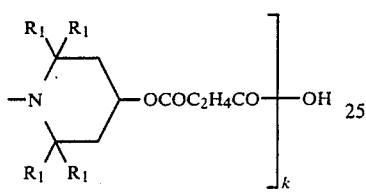  [II]

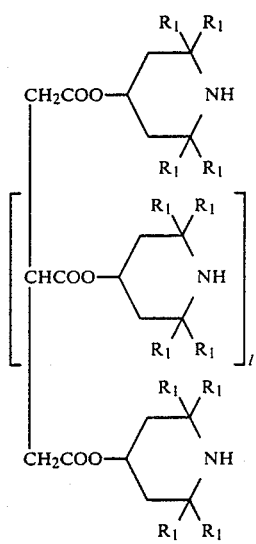

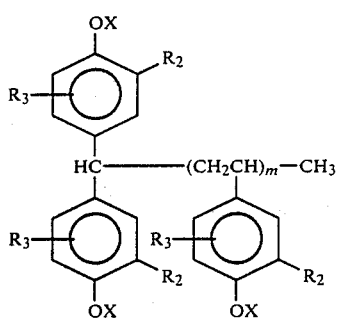  [III]

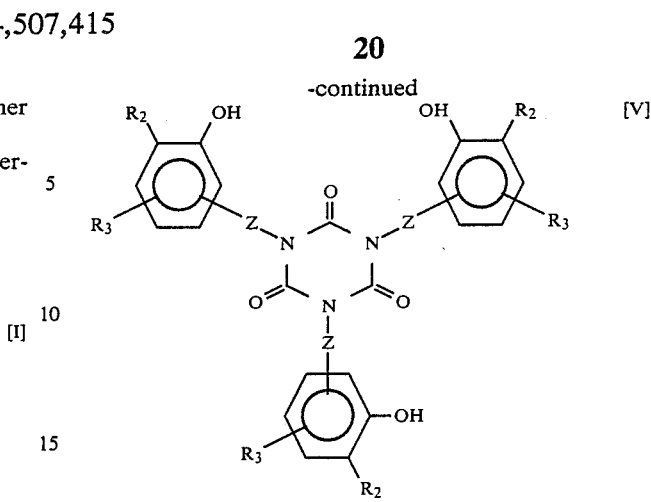  [V]

wherein:
$R_1$ represents an alkyl group containing 1–12 carbon atoms;
$R_2$ represents an alkyl group containing 3–12 carbon atoms;
$R_3$ represents an alkyl group containing 1–18 carbon atoms;
X represents hydrogen atom or the group

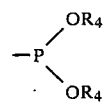

in which $R_4$ is an alkyl group containing 1–30 carbon atoms;
Y represents a divalent hydrocarbon radical containing 1–18 carbon atoms or sulfur atom; P1 Z represents a divalent hydrocarbon radical containing 1–8 carbon atoms in which a carbonyloxy group may be interposed;
k is an integer of 1–10;
l is an integer of 1–16; and
m is an integer of 1–6.

2. A medical article according to claim 1 molded from a composition comprising as the stabilizers from 0.03 to 0.3 part by weight of a hindered amine represented by the aforementioned formula [I] or [II] and from 0.02 to 0.2 part by weight of a phenol or its phosphite ester compound represented by the aforementioned formula [III], or [V] per 100 parts by weight of a propylene polymer with a weight-average molecular-weight to number average molecular-weight ratio of 2.5–4.8.

3. A medical article according to claim 1 or 2 wherein said hindered amine is a compound represented by said formula [I] in which $R_1$ is methyl and k is 3 or 4.

4. A medical article according to claim 1 or 2 wherein said hindered amine is a compound represented by said formula [II] in which $R_1$ is methyl and l is 2.

5. A medical article according to claim 1 wherein said phenol compound is a compound represented by said formula [III] in which $R_2$ is t-butyl (5-position), $R_3$ is methyl (2-position), X is hydrogen atom and m is 1.

6. A medical article according to claim 1 wherein said phenol phosphite ester compound is a compound represented by said formula [III] in which $R_2$ is t-butyl (5-positon), $R_3$ is methyl, X is the group—$P(OC_{18}H_{37})_2$ and m is 1.

7. A medical article according to claim 1 wherein said phenol compound is a compound represented by said formula [V] in which $R_2$ and $R_3$ each are t-butyl (3- and 5-positions) and Z is methylene.

8. A medical article according to claim 1 wherein said molded articles are injection-molded products.

9. A medical article according to claim 8 wherein said injection-molded products are syringes, needle bases for the syringe, infusion or blood transfusion set or instruments for blood collection.

10. A medical article according to claim 1 molded from a composition additionally containing from 0.01 to 0.4 part by weight of a compound represented by the formula [VI] below as the nucleating agent in said composition.

13. A medical article according to claim 2 wherein said hindered amine is a compound represented by said formula [I] in which $R_1$ is methyl and k is 3 or 4 or a compound represented by said formula [II] in which $R_1$ is methyl and l is 2; and said phenol compound is a compound represented by (i) said formula [III] in which $R_2$ is t-butyl (5-position), $R_3$ is methyl (2-position), X is hydrogen atom and m is 1 or (ii) said formula [III] in which $R_2$ is t-butyl (5-position), $R_3$ is methyl, X is the group $—P(OC_{18}H_{37})_2$ and m is 1.

14. A medical article according to claim 13 molded from a composition additionally containing from 0.01 to 0.4 part by weight of a compound represented by the formula (VI) below as the nucleating agent in said composition

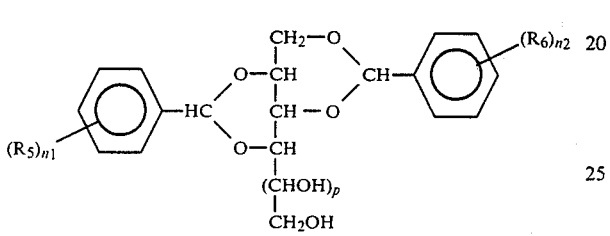

[VI]

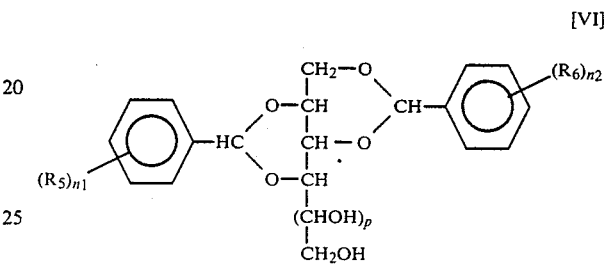

[VI]

in which $R_5$ and $R_6$ each represent an alkyl or alkoxy group containing 1–8 carbon atoms, hydroxyl group or a halogen atom, $n_1$ and $n_2$ each independently represent an integer of 1–3 and p represents 0 or 1.

11. A medical article according to claim 10 molded from a composition additionally containing from 0.05 to 0.3 part by weight of a compound represented by said formula [VI] as the nucleating agent.

12. A medical article according to claims 10 or 11 wherein said nucleating agent is a compound of said formula [VI] in which $R_5$ and $R_6$ each are methyl (4-position), $n_1$ and $n_2$ each are 1 and p is 1.

in which $R_5$ and $R_6$ each represent an alkyl or alkoxy group containing 1–8 carbon atoms, hydroxyl group or a halogen atom, $n_1$ and $n_2$ each independently represent an integer of 1–3 and p represents 0 or 1.

15. A medical article according to claim 2 wherein said hindered amine is a compound represented by said formula [I] in which $R_1$ is methyl and k is 3 or 4 or a compound represented by said formula [II] in which $R_1$ is methyl and l is 2; and said phenol compound is a compound represented by said formula [V] in which $R_2$ and $R_3$ each are t-butyl (3- and 5-positions) and Z is methylene.

* * * * *

UNITED STATES PATENT AND TRADEMARK OFFICE
CERTIFICATE OF CORRECTION

PATENT NO. : 4,507,415  PAGE 1 OF 3.
DATED : March 26, 1985
INVENTOR(S) : Masaaki KASAI et al It is certified that error appears in the above-identified patent and that said Letters Patent is hereby corrected as shown below:

Column 6, line 2, change "-CH-CH$_2$-CH$_2$-CH$_3$" to

-->CH-CH$_2$-CH$_2$-CH$_3$--.

Column 7, line 27, change "horus" to --hours--.

Column 8, line 30, change "Examwple" to --Example--.

Column 10, after the last line, before "TABLE 2", insert the sentence

--Results of the tests are shown in TABLE 3.--.

Columns 9 and 10, TABLE 3, under "Example 2, (1)" change

"32.5°" to --32.5--.

UNITED STATES PATENT AND TRADEMARK OFFICE
CERTIFICATE OF CORRECTION

PATENT NO. : 4,507,415           PAGE 2 OF 3.
DATED : March 26, 1985
INVENTOR(S) : Masaaki KASAI et al It is certified that error appears in the above-identified patent and that said Letters Patent is hereby corrected as shown below:

Columns 9 and 10, TABLE 3, under "Example 2, (2)"

change "-°" to -- - --.

Columns 9 and 10, TABLE 3, under "Comparative Example 2, (6)" change "°°" to -- - --.

Columns 13 and 14, TABLE 4, under "Comparative Example 3, (2)" change "±" to -- (±) --.

Column 14, line 53, change "small" to --smell--.

Column 16, line 62, change "odorles" to --odorless--.

Columns 17 and 18, TABLE 6, under "Example 5 and

UNITED STATES PATENT AND TRADEMARK OFFICE
CERTIFICATE OF CORRECTION

PATENT NO. : 4,507,415
DATED : March 26, 1985
INVENTOR(S) : Masaaki KASAI et al

It is certified that error appears in the above-identified patent and that said Letters Patent is hereby corrected as shown below:

Comparative Example 5", under all columns, line 25, insert --0--.

Column 20, line 36, delete "P1".

Signed and Sealed this

Thirteenth Day of January, 1987

Attest:

DONALD J. QUIGG

Attesting Officer    Commissioner of Patents and Trademarks